United States Patent
Adams et al.

(12) 
(10) Patent No.: US 6,302,311 B1
(45) Date of Patent: *Oct. 16, 2001

(54) ENDOSCOPIC STAPLER

(75) Inventors: Ronald David Adams, Holliston, MA (US); Lauren O. Main, Loveland, OH (US); Scott E. Swaffar, Bloomington, IN (US); Charles H. Pugsley, Jr., Pelham, NH (US); David P. Gordon, Stamford, CT (US)

(73) Assignee: Boston Scientific Corporation, Natick, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/633,113

(22) Filed: Aug. 4, 2000

Related U.S. Application Data

(63) Continuation of application No. 08/662,659, filed on Jun. 14, 1996, now Pat. No. 6,119,913.

(51) Int. Cl.[7] .................................................. A61B 17/068
(52) U.S. Cl. ..................... 227/176.1; 227/19; 227/178.1; 227/180.1
(58) Field of Search .............................. 227/176.1, 178.1, 227/180.1, 19, 175.1

(56) References Cited

U.S. PATENT DOCUMENTS

| | | |
|---|---|---|
| 4,047,654 | 9/1977 | Alvarado . |
| 4,261,346 | 4/1981 | Wettermann . |
| 4,319,576 | 3/1982 | Rothfuss . |
| 4,473,077 | 9/1984 | Noiles et al. . |
| 4,485,817 | 12/1984 | Swiggert . |
| 4,488,523 | 12/1984 | Shichman . |
| 4,576,167 | 3/1986 | Noiles . |
| 4,576,846 | 3/1986 | Noel . |
| 4,646,722 | 3/1987 | Silverstein et al. . |
| 4,671,445 | 6/1987 | Barker et al. . |
| 4,747,833 | 5/1988 | Kousai et al. . |
| 4,754,909 | 7/1988 | Barker et al. . |
| 4,776,506 | 10/1988 | Green . |
| 4,817,847 | 4/1989 | Redtenbacher et al. . |

(List continued on next page.)

FOREIGN PATENT DOCUMENTS

| | | |
|---|---|---|
| 442588 | 8/1991 | (EP) . |
| 93/15668 | 8/1993 | (WO) . |
| 96/18344 | 6/1996 | (WO) . |

*Primary Examiner*—Scott A. Smith
(74) *Attorney, Agent, or Firm*—Kenyon & Kenyon

(57) ABSTRACT

An endoscopic stapler includes a stapling head which is removably locatable on the distal end of an endoscope. The stapling head includes a stationary part which houses a removable staple cartridge and a movable part which includes an anvil for receiving and bending the ends of staples fired from the stationary part. The staple cartridge preferably houses two semi-circular rows of staples which are staggered relative to each other. The movable part is coupled to the stationary part by a threaded shaft which engages a worm gear in the stationary part and a first rotatable control wire is coupled to the worm gear. A substantially semi-circular firing cam is located proximal of the staple cartridge in the stationary part. The firing cam has an interior splined surface which is engaged by a spline gear coupled to a second rotatable control wire. In one embodiment, a knife is coupled to the firing cam so that tissue is cut subsequent to stapling. In another embodiment, laser-optical paths are provided for cutting tissue after stapling. The proximal end of the stapling head is coupled to a sleeve having lumen for the control wires and a lumen for a standard endoscope. In another embodiment, a modified endoscope is provided with lumena for the control cables. The modified endoscope is removably attached to the stapling head by either a screw connection or a snap connection.

8 Claims, 10 Drawing Sheets

U.S. PATENT DOCUMENTS

| | | |
|---|---|---|
| 5,005,749 | 4/1991 | Aranyi . |
| 5,015,249 | 5/1991 | Nakao et al. . |
| 5,025,778 | 6/1991 | Silverstein . |
| 5,049,153 | 9/1991 | Nakao et al. . |
| 5,088,979 | 2/1992 | Filipi et al. . |
| 5,156,609 | 10/1992 | Nakao et al. . |
| 5,193,731 | 3/1993 | Aranyi . |
| 5,197,649 | 3/1993 | Bessler et al. . |
| 5,217,001 | 6/1993 | Nakao et al. . |
| 5,219,111 | 6/1993 | Bilotti et al. . |
| 5,226,876 | 7/1993 | Filipi et al. . |
| 5,251,801 | 10/1993 | Ruckdeschel et al. . |
| 5,258,008 | 11/1993 | Wilk . |
| 5,259,366 | 11/1993 | Reydel et al. . |
| 5,261,920 | 11/1993 | Main et al. . |
| 5,271,543 | 12/1993 | Grant et al. . |
| 5,271,544 | 12/1993 | Fox et al. . |
| 5,275,322 | 1/1994 | Brinkerhoff et al. . |
| 5,285,945 | 2/1994 | Brinkerhoff et al. . |
| 5,314,435 | 5/1994 | Green et al. . |
| 5,333,773 | 8/1994 | Main et al. . |
| 5,360,154 | 11/1994 | Green . |
| 5,383,880 | 1/1995 | Hoovan . |
| 5,403,326 | 4/1995 | Harrison et al. . |
| 5,433,721 | 7/1995 | Hooven et al. . |
| 5,437,637 | 8/1995 | Lieber et al. . |
| 5,437,684 | 8/1995 | Calabrese et al. . |
| 5,443,198 | 8/1995 | Viola et al. . |
| 5,445,644 | 8/1995 | Pietrafitta et al. . |
| 5,447,514 | 9/1995 | Gerry et al. . |
| 5,454,825 | 10/1995 | Van Leeuwen et al. . |
| 5,465,894 | 11/1995 | Clark et al. . |
| 5,474,223 | 12/1995 | Viola . |
| 5,868,760 | 2/1999 | McGuckin, Jr. . |
| 6,119,913 * | 9/2000 | Adams et al. ............. 227/176.1 |

* cited by examiner

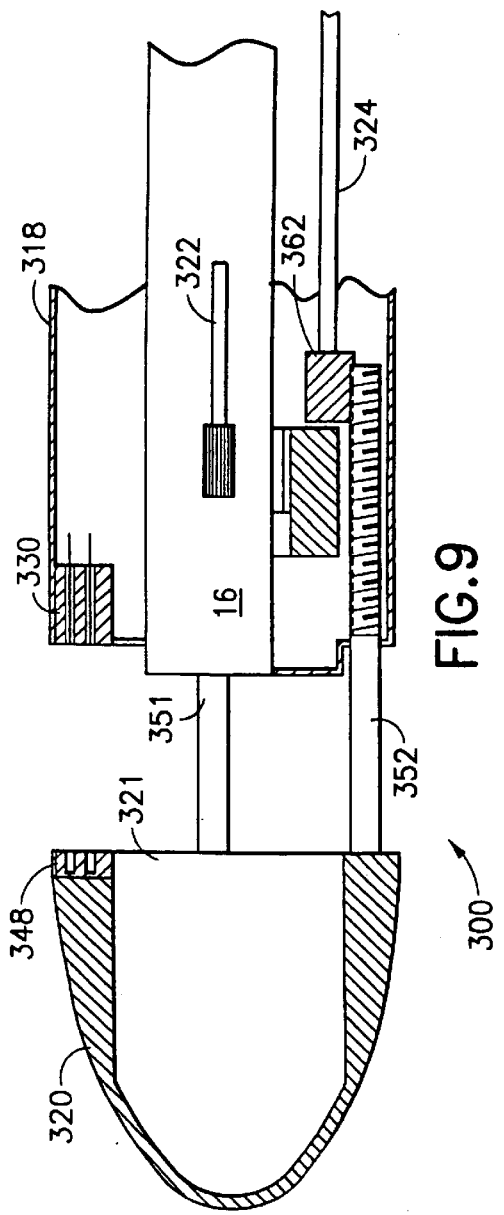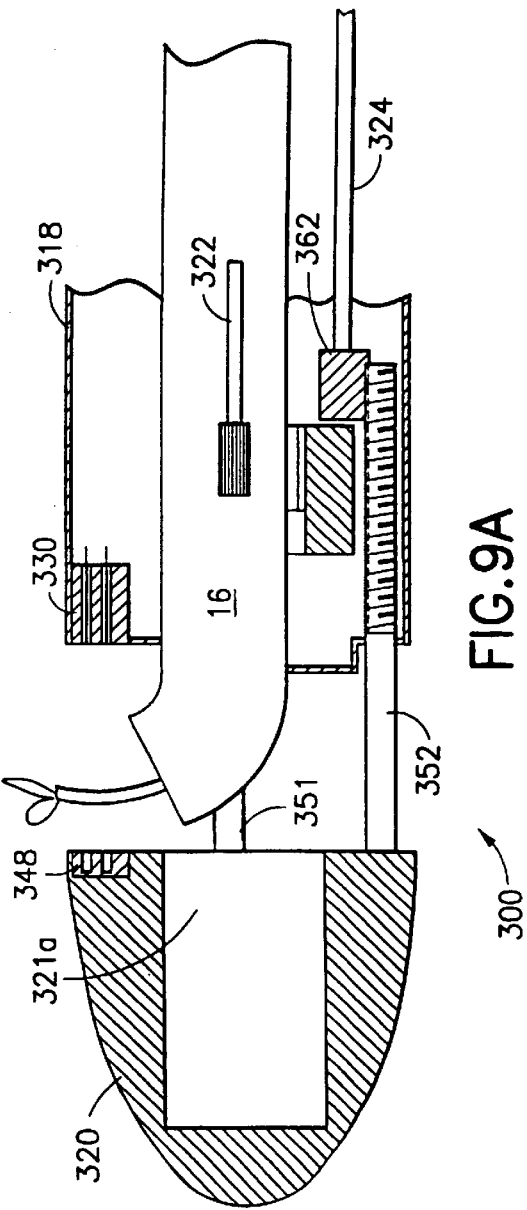

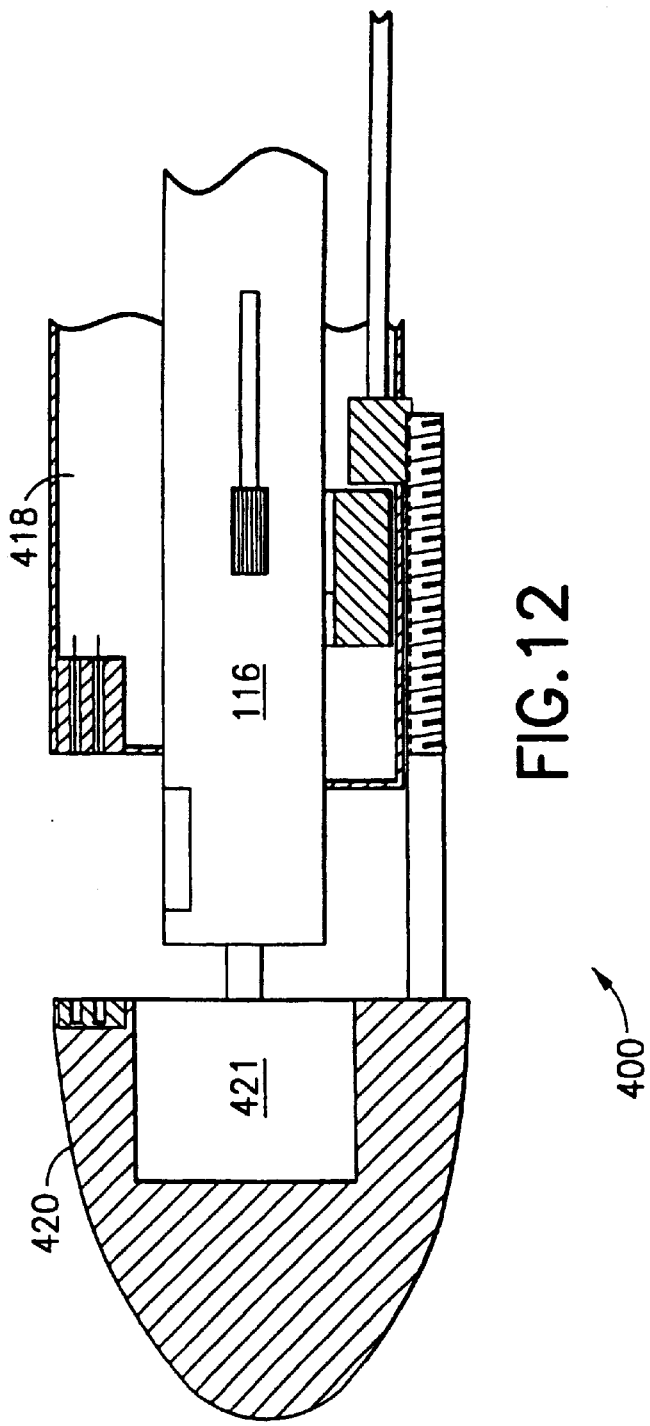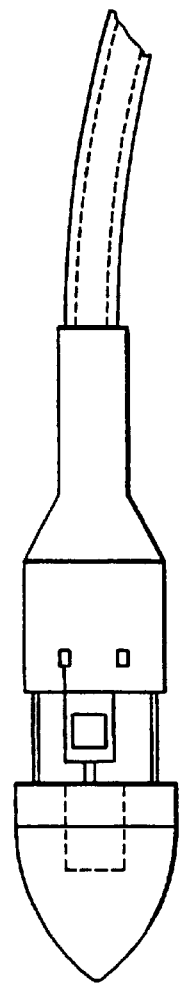

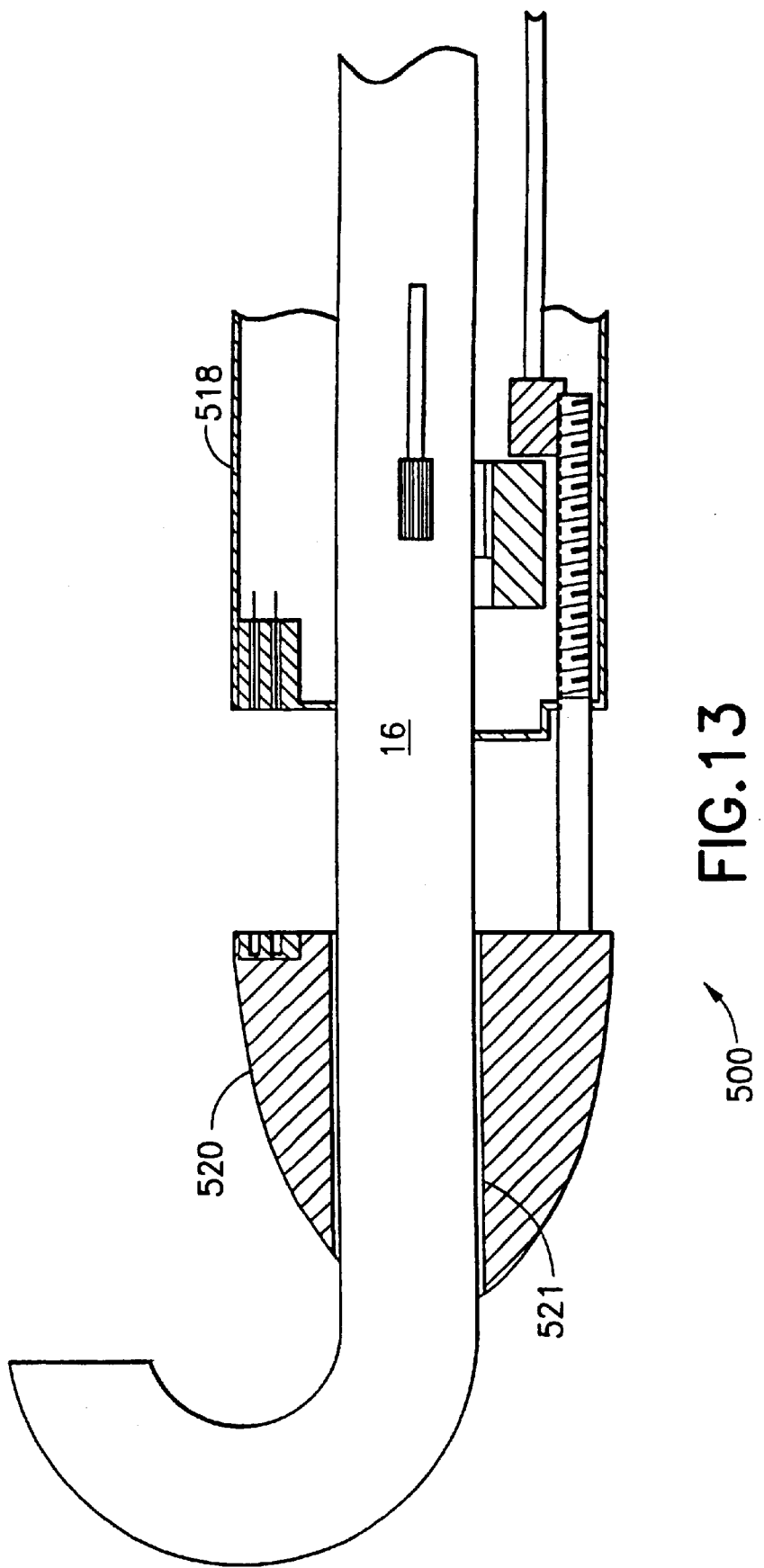

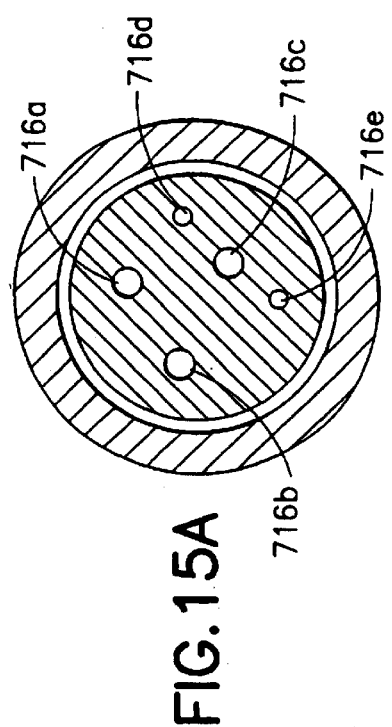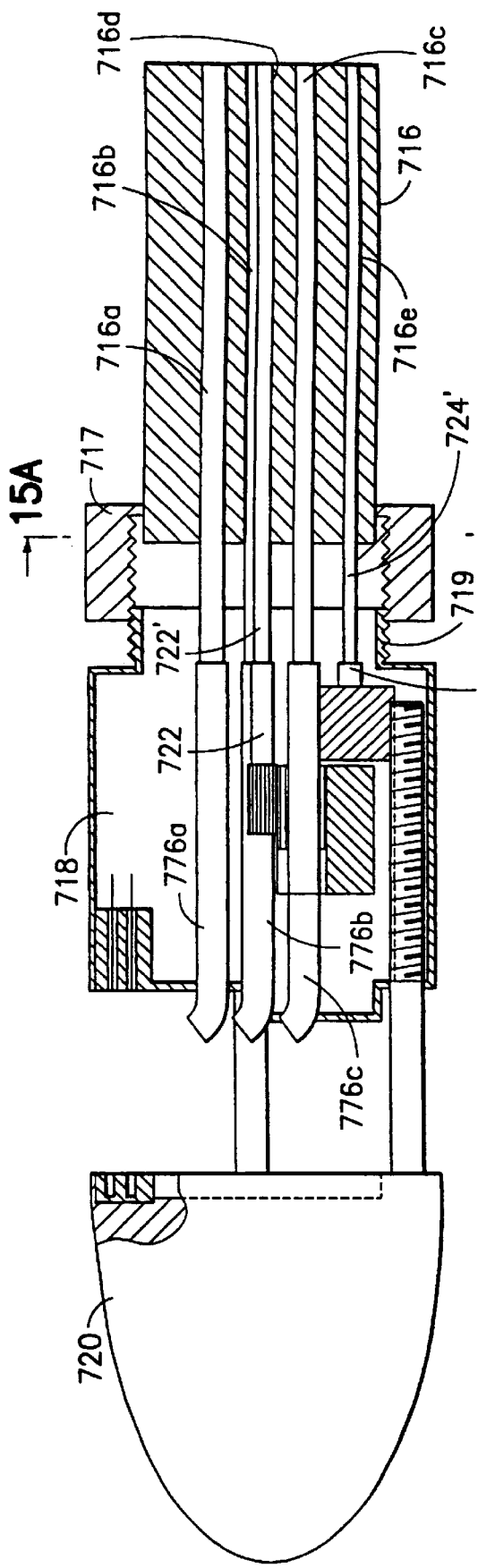

ENDOSCOPIC STAPLER

This application is a continuation of Ser. No. 08/662,659 filed Jun. 14, 1996 now U.S. Pat. No. 6,119,913.

BACKGROUND OF THE INVENTION

1. Field of the Invention

The present invention relates generally to a surgical stapler for applying surgical staples to tissue. More particularly, the present invention relates to a surgical stapler which is attached to an endoscope. The present invention has particular application to transanal or transoral surgical procedures, although it is not limited thereto.

2. State of the Art

It has been long known in the surgical arts that surgical staplers provide an expeditious and efficient way of joining or repairing tissue. In fact, in certain types of surgical procedures, the use of surgical staples has become the preferred method of joining tissue as opposed to suturing. A common use of surgical staplers relates to the repair of the colon after a portion of the colon has been removed. For example, when a tumor is found in the colon, it is not uncommon to remove a large portion of the colon. The remaining sections of the colon are then joined together in a surgical procedure called anastomosis, where the tubular sections are joined together to form a continuous tubular pathway.

In the anastomosis procedure, the abdominal cavity of the patient is typically opened to expose the diseased portion of the colon. The diseased portions of the colon are then surgically removed, and the remaining portions of the colon are joined together. Prior to the use of staplers, the anastomosis procedure was laborious and lengthy as the surgeon had to cut and precisely align the ends of the intestine and maintain the alignment while joining the ends with sutures. The development of circular staplers greatly simplified the anastomosis procedure by permitting the surgeon to simultaneously provide one or more rows of staples which join sections of the colon while cutting away excess tissue which would otherwise occlude the tubular passageway. However, even with the use of the circular stapler, it is still necessary to create an access port in an otherwise healthy portion of the colon for entry and removal of the stapler. After the stapler is used for anastomosis, and then removed from the colon through the access port, it is necessary to repair the colon at the access port via suturing or linear stapling.

Many different circular staplers are known in the art, and several are commercially available. For example, circular staplers are sold under the PROXIMATE brand by Ethicon Inc., Somerville, N.J. such as are described in U.S. Pat. No. 5,205,459 to Brinkerhoff et al., U.S. Pat. No. 5,261,920 to Main et al., U.S. Pat. No. 5,271,544 to Fox et al., U.S. Pat. No. 5,285,945 to Brinkerhoff et al., U.S. Pat. No. 5,333,773 to Main et al, and U.S. Pat. No. 5,445,644 to Pietrafitta et al., all of which are hereby incorporated by reference herein in their entireties. Other circular staplers are sold under the AUTO SUTURE brand by United States Surgical Corporation, Norwalk, Conn. and are described in U.S. Pat. No. 4,576,167 to Noiles, U.S. Pat. No. 5,005,749 to Aranhi, U.S. Pat. No. 5,193,731 to Aranyi, No. U.S. Pat. No. 5,360,154 to Green, U.S. Pat. No. 5,443,198 to Viola et al., U.S. Pat. No. 5,437,684 to Calabrese et al., U.S. Pat. No. 5,447,514 to Gerry et al., U.S. Pat. No. 5,454,825 to Van Leeuwen et al., and U.S. Pat. No. 5,474,223 to Viola et al., all of which are also hereby incorporated by reference herein in their entireties. Generally common to all circular staplers are several elements, including a staple head assembly, a shaft assembly, and a handle assembly. The staple head assemblies all include a staple holder which holds a plurality of staples arranged around a circular periphery, a circular anvil which acts to form the ends of staples driven through the tissue, a circular knife or scalpel, and a driver which drives the staples from the staple holder and actuates the knife. The shaft assembly typically includes a substantially rigid longitudinally curved shaft which holds a tension member for transmitting tension from an actuator handle to the anvil to resist forces on the anvil, a compression member for transmitting a compressive force from the actuator handle assembly for advancing the staple driver to drive the staples into the tissue and to drive the knife through the tissue adjacent the staples. The handle assembly typically includes a handle, and one or more levers and/or knobs. The levers and knobs are used for moving the anvil relative to the staple holder, and for firing the staples and the knife.

While great improvements in circular staplers have been made over the years, it will be appreciated by those skilled in the art that the anastomosis procedure is still an extremely invasive procedure which leaves both external and internal scars. Indeed, not only must the abdominal cavity be opened, but a large segment of the colon is typically removed to avoid the possibility of recurrence, as recurrence would lead to another traumatic surgery. Moreover, as described above, the colon must be punctured at a healthy location to provide a port for the circular stapler, and this puncture must then be sutured or stapled (as must the abdominal cavity).

Clearly, it is desirable to avoid excessive trauma to healthy portions of the colon during the anastomosis procedure. Toward that end, various flexible surgical staplers have been proposed which theoretically can be introduced transanally such that the colon need not be punctured at a healthy location to provide an access port for the stapler. These flexible shaft staplers are disclosed inter alia in U.S. Pat. No. 4,671,445 to Barker et al., U.S. Pat. No. 4,473,077 to Noiles et al., U.S. Pat. No. 4,488,523 to Shichman, U.S. Pat. No. 4,754,909 to Barker et al., U.S. Pat. No. 5,258,008 to Wilk, U.S. Pat. No. 5,271,543 to Grant et al., and U.S. Pat. No. 5,433,721 to Hooven et al., and PCT application WO 93/15668 to Blanco et al., all of which are incorporated by reference herein in their entireties. While these flexible shaft staplers provide one advantage, they do not obviate the need for abdominal surgery, as when the stapler is in place, there is no manner of viewing the surgical site other than via laparoscopic or open abdominal surgery. In addition, the flexible shaft staplers suffer from other shortcomings. In particular, some of the flexible shaft staplers do not have long shafts which would permit them to reach well up into the colon. Others of the flexible shaft staplers have shaft assemblies which are cumbersome and/or impractical and expensive to build. Others of the flexible shaft staplers have stiffening problems due to the force required for the simultaneous firing of multiple staples which are circumferentially disposed. Regardless of the particular nature of the shortcomings, they have apparently been such that the flexible shaft staplers have not been commercially successful.

In a similar vein to the flexible surgical staplers is U.S. Pat. No. #5,197,649 to Bessler et al. which is hereby incorporated by reference herein in its entirety, and which provides a steerable endoscopic stapler which is introduced via the rectum, but which requires that the diseased portion of the colon be already removed using invasive surgical tools. The steerable endoscopic stapler of Bessler et al. proposes a custom instrument which includes the basic steering and ocular capabilities of a standard endoscope, a circular staple head assembly at the distal end of the endoscope, and a cable and pulley system for bringing the anvil and stapler of the staple head together and firing the staples and knife. While the concept of combining the visual apparatus of the endoscope with the stapler in a single device has certain advantages, it will be appreciated by those skilled in the art that an entire re-engineering of the commonly used endoscopes is undesirable. Indeed, staplers are typically disposable instruments because of difficulties in cleaning and controlling critical dimensions, while endoscopes are very expensive reusable instruments. A combination instrument as proposed by Bessler et al. would therefore be economically unfeasible as cleaning and sterilization of the device would be impossible. In addition, the mechanics of the device proposed by Bessler et al. has numerous drawbacks which make it impractical. For example, while the single cable and pulley system will ostensibly work to bring the anvil and stapler together and then fire the staples and knife, there is no mechanism provided for opening the anvil relative to the stapler after stapling. Further, while no sizes are mentioned, it would appear (by comparing the relative sizes of the flexible endoscope shaft portion and the head portions) that the head portion of the stapler is undesirably large (e.g., three times as large as the flexible shaft), and would present major steering problems. Finally, it is impossible to perform a full 360° anastomosis endoluminally without the aid of other surgical techniques. One side of the exterior surface of the bowel is attached to the mesenteric vascular arcade which must be detached from the bowel before performing anastomosis. There is no known way to perform the detachment other than via open or laparoscopic surgery.

In order to avoid the trauma of abdominal surgery completely, it has been suggested that a flexible endoscopic stapler be provided over an endoscope, such that both the stapler and endoscope are introduced via the rectum and no incisions are required. Such a flexible endoscopic stapler would include a head assembly, a flexible tubular member, and a proximal control assembly. The flexible tubular member would include numerous lumena, including a large lumen for receiving a standard type endoscope which moves relative to the stapler, and smaller lumena for receiving forceps instruments, cables, steering elements for the head assembly, etc. The head assembly would include a clamshell (elongated truncated ellipsoid) shaped stapler head and a similarly shaped anvil which are hinged relative to each other. The staples would be located in a cartridge placed in the stapler head, and assume two rows forming a quarter circle curve and a straight line extending from the quarter circle curve. The anvil would be provided with a similar configuration. A knife would moves along a similarly shaped track inside of the staples. The stapler head would moved relative to the anvil (or vice versa) utilizing a cable and pulley arrangement in conjunction with a bevel gear. The proposed device would not be intended to perform an anastomosis, but rather would provide a full tissue resection and stapling repair of a smaller portion of the colon without requiring invasive abdominal surgery (i.e., an incision). It is believed that full tissue resections of the diseased portions of the colon should be a sufficient treatment where invasive abdominal surgery can be avoided, as the treatment is less traumatic and can be repeated if necessary.

While the proposed full tissue resection device would provide a conceptual improvement over the prior art, it would still suffer from several drawbacks. First, a clamshell shaped arrangement with a hinged stapler head and anvil is non-optimal for several reasons. First, with a hinged arrangement, tissue is forced outward from the stapler as the stapler is closing, thereby risking a failure to obtain the desired tissue. Second, with the hinged arrangement the overall diameter of the clamshell and the stapler device is increased dramatically when the stapler is opened, thereby risking tearing of non-diseased tissue. Third, alignment of the staples with the receivers in the anvil is extremely difficult because the stapler head and anvil will not always close to the same location (i.e., depending on the amount and density of the tissue trapped therebetween). In addition, with a clamshell shaped hinged stapler, the mechanics of the stapler head are at best difficult and unwieldy. In particular, the stapler arrangement with a curved section and a straight section leads to issues regarding the shape of the knife and the staple driver. Likewise, the cable and pulley arrangement with the bevel gear for opening and closing the stapler head is extremely complex and consumes large amounts of space within the device. Further, it will be appreciated that because of all of the mechanical issues, the head of such a stapler device would be extremely large and unlikely to be able to be steered significantly into the colon. Finally, it will be appreciated that because the complexities of such a device, including the steering abilities, etc., the cost of manufacturing a disposable device would be extremely large, thus reducing the likelihood of its commercial acceptance.

SUMMARY OF THE INVENTION

It is therefore an object of the invention to provide a endoscopic stapler.

It is another object of the invention to provide an endoscopic stapler for use in a full thickness tissue resection procedure.

It is a further object of the invention to provide an endoscopic stapler which may be removably fitted around or onto a standard endoscope.

It is an additional object of the invention to provide an endoscopic stapler which can be used in conjunction with an endoscope to provide a full thickness tissue resection without invasive abdominal surgery.

It is also an object of the invention to provide an endoscopic stapler having a semicircular anvil and a semicircular arrangement of sequentially fired staples.

Another object of the invention is to provide an endoscopic stapler having a stapler head having a diameter no larger than 30 mm which can be directed well into the colon, or well past the stomach.

A further object of the invention is to provide an endoscopic stapler having an anvil and a stapler head which move axially relative to each other.

An additional object of the invention is to provide an endoscopic stapler which is attached to an endoscope and which permits endoscopic viewing of the surgical site at the head of the endoscopic stapler.

It is yet another object of the invention to provide a disposable endoscopic stapler which is relatively inexpensive to manufacture, and easy to use.

It is even an additional object of the invention to provide an endoscopic stapler with simple head closure and staple firing mechanisms.

Yet a further object of the invention is to provide an endoscopic stapler for removable attachment to the distal end of a modified endoscope.

In accord with these objects which will be discussed in detail below, an endoscopic stapler according to the invention broadly includes a stapling head which is removably locatable on the distal end of an endoscope. The stapling head includes a stationary part which houses a removable staple cartridge and a movable part which includes an anvil for receiving and bending the ends of staples fired from the stationary part. According to a presently preferred embodiment, the staple cartridge houses two semi-circular rows of staples which are staggered relative to each other. The movable part is coupled to the stationary part by a threaded shaft which engages a worm gear in the stationary part and a first rotatable control wire is coupled to the worm gear. A substantially semi-circular firing cam is located proximal of the staple cartridge in the stationary part. The firing cam has an interior splined surface which is engaged by a spline gear coupled to a second rotatable control wire. In one embodiment of the invention, a knife is coupled to the firing cam so that tissue is cut subsequent to stapling. In another embodiment of the invention, laser-optical paths are provided adjacent to the staple cartridge for cutting tissue after stapling.

According to one embodiment of the invention, the proximal end of the stapling head is coupled to a sleeve having lumens for the control wires and a lumen for a standard endoscope. In another embodiment of the invention, a modified endoscope is provided with lumen for the control cables. The modified endoscope is removably attached to the stapling head by either a screw connection or a snap connection. The proximal ends of the control wires are thereby located near the proximal end of the endoscope and are attached to a device for rotating the cables.

Additional objects and advantages of the invention will become apparent to those skilled in the art upon reference to the detailed description taken in conjunction with the provided figures.

BRIEF DESCRIPTION OF THE DRAWINGS

FIG. 9 is a view similar to FIG. 2 of a second embodiment of the invention;

FIG. 9a is a view similar to FIG. 9 showing the invention used with and endoscope having an articulate distal end;

FIG. 12 is a view similar to FIG. 9 of an alternate second embodiment of the invention;

FIG. 12A is a view similar to FIG. 8 of the embodiment of FIG. 12;

FIG. 13 is a view similar to FIG. 12 of a third embodiment of the invention;

FIG. 15 is a view similar to FIG. 14 of a fifth embodiment of the invention; and FIG. 15a is a sectional view taken along line 15A—15A in FIG. 15.

DETAILED DESCRIPTION OF THE PREFERRED EMBODIMENTS

Figure 1:
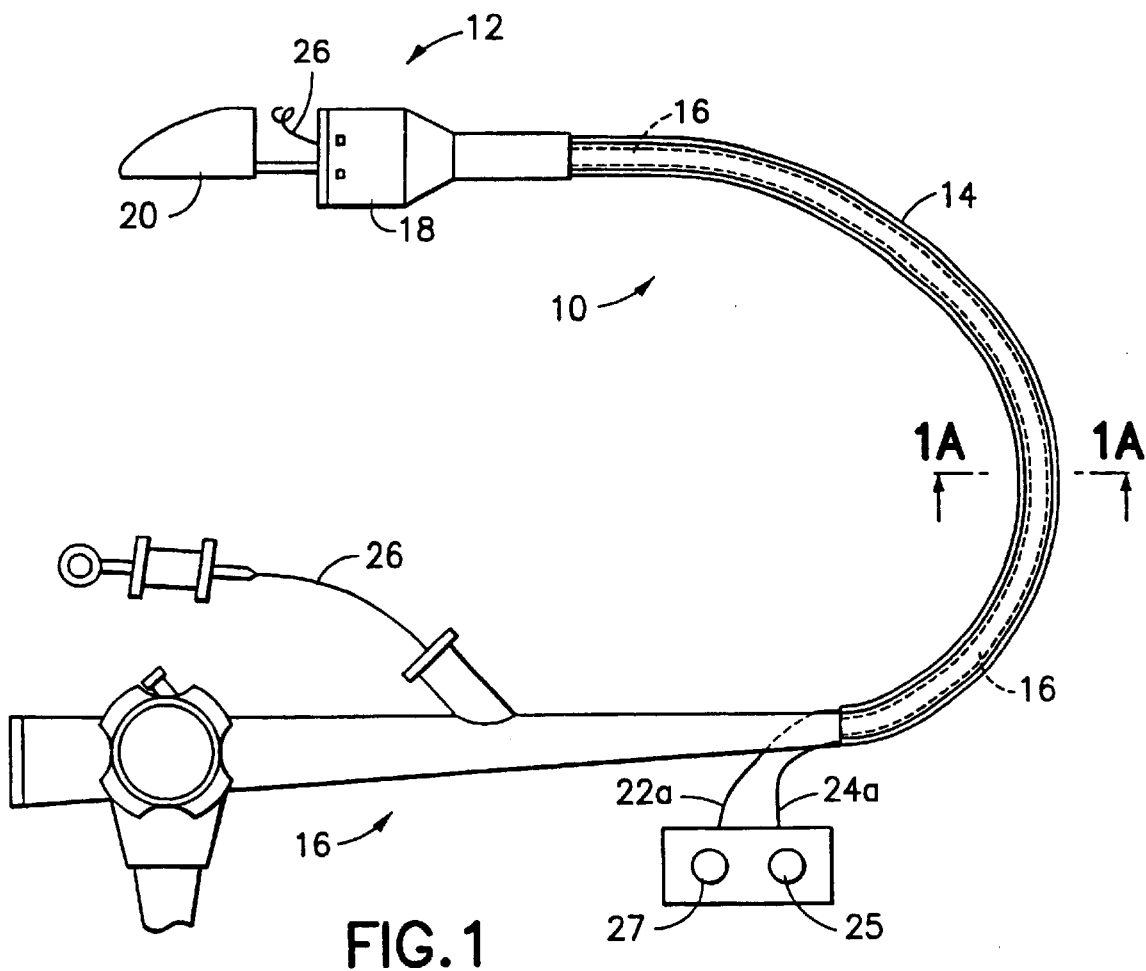
FIG. 1 is a perspective view of a first embodiment of an endoscopic stapler according to the invention.
Figure 1A:
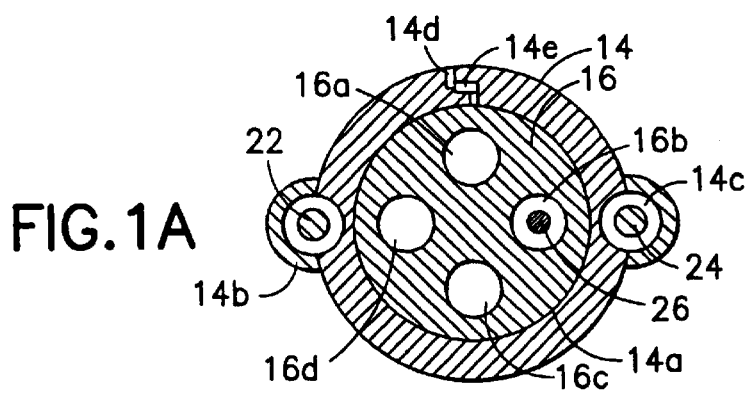
FIG. 1A is a sectional view taken along line 1A—1A in FIG. 1.
Figure 2:
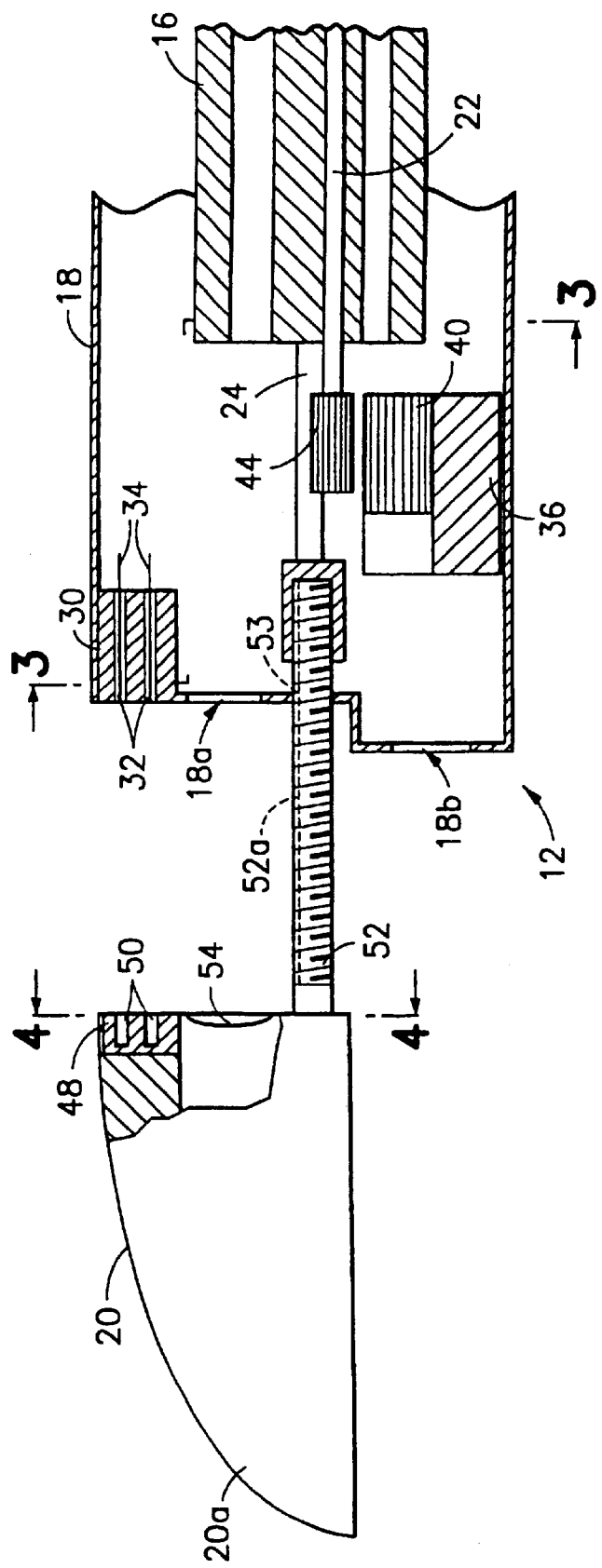
FIG. 2 is an enlarged, broken, partially transparent longitudinal section of the distal stapler head of the stapler of FIG. 1.
Figure 4:
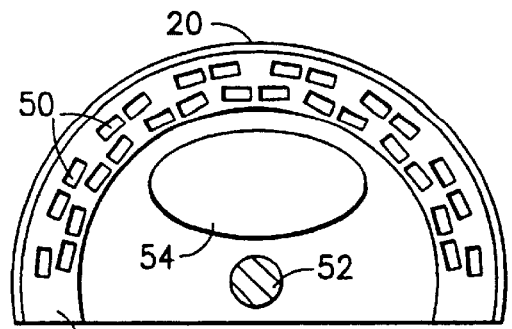
FIG. 4 is a proximal end view looking in the direction 4—4 in FIG. 2.
Figure 3:
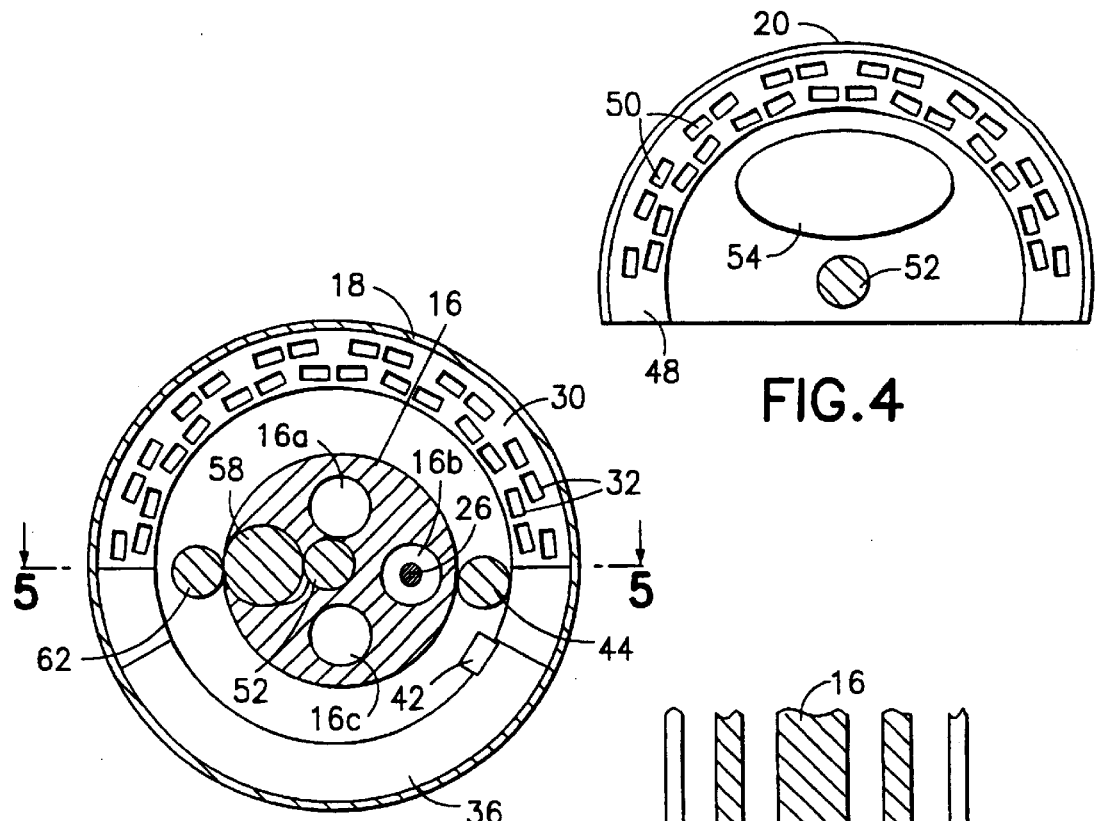
FIG. 3 is a sectional view taken along line 3—3 in FIG. 2.
Figure 5:
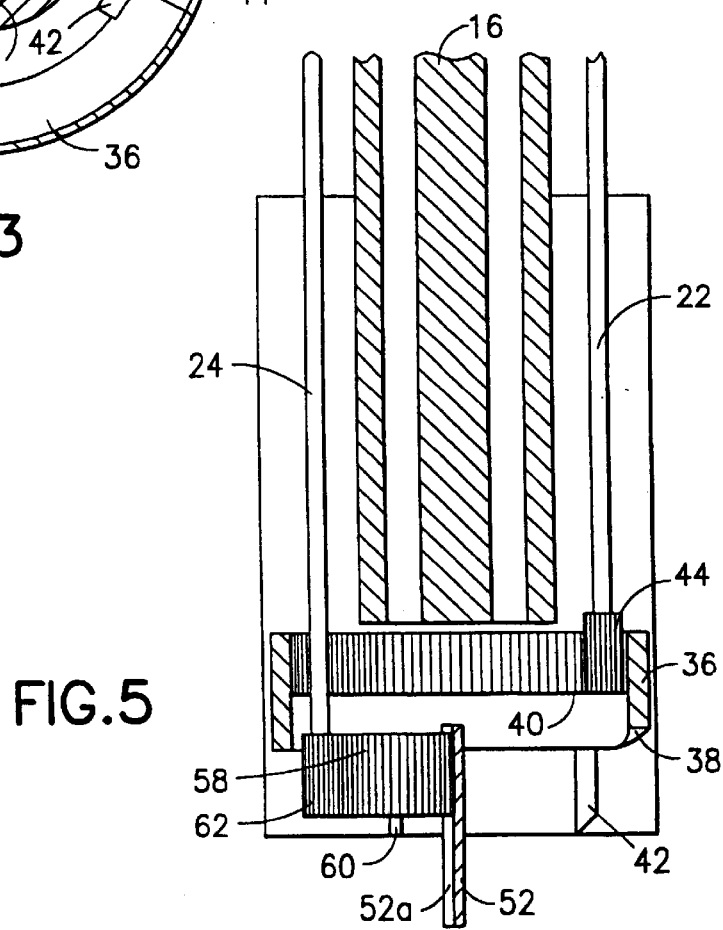
FIG. 5 is a sectional view taken along line 5—5 in FIG. 3.

Turning now to FIGS. 1 and 1a, an endoscopic stapler 10 according to the preferred embodiment of the invention generally includes a stapling head 12 with an attached sleeve 14 for attaching the stapler 10 to a conventional endoscope 16. The stapler head 12 has a stationary part 18 and a movable part 20 which are described in more detail below with reference to FIGS. 2–5. Generally, however, according to the preferred embodiment of the invention, the movable part 20 is moved by rotating a flexible torsionally rigid control wire and the stationary portion 18 is operated by rotating a similar flexible torsionally rigid control wire 24.

As seen best in FIG. 1a, the sleeve 14 has a central lumen 14a and two outer or side lumens 14b and 14c. The center lumen 14a is easily accessed by a longitudinal slit 14d which preferably includes interlocking means 14e. The side lumens 14b and 14c carry the control wires 22 and 24 respectively. As seen in FIG. 1, the proximal ends of the control wires 22 and 24 exit the lumens 14b, 14c and are coupled to rotating means 25, 27 for rotating the control wires as described below. The rotating means 25, 27 may be ratcheted hand wheels, knobs, electric motors, rack and pinion foot pedals, etc., or any combination thereof.

Referring once again to both FIGS. 1 and 1a, the stapler 10 is attached to a conventional endoscope 16 by inserting the endoscope 16 into the sleeve 14 via the slit 14d so that the distal end of the endoscope resides inside the stationary part 18 of the stapling head 12 as shown and described below. The endoscope 16 is advantageously provided with four ports 16a–16d, two of which (e.g. 16a and 16c) provide optical paths and two of which (e.g. 16b and 16d) provide lumens for instrumentation. Those skilled in the art will appreciate that the ports of the endoscope are shown schematically in FIG. 1a and that different endoscopes may have different, although similar, arrangements of ports. Likewise, it will be appreciated that the sleeve 14 is shown schematically in FIG. 1a and may be of different thicknesses with different numbers and locations of lumens.

In order to facilitate a full tissue resection operation by the stapler, a forceps instrument 26 may be inserted through a lumen (e.g. 16b) of the endoscope 16 into the space between the stationary part 18 and the movable part 20 of the stapler head in order to pull tissue into the stapler as described in more detail below. The forceps instrument 26 may be a conventional forceps instrument or an articulating forceps such as is described in U.S. Pat. No. 4,880,015 to Nierman, the complete disclosure of which is hereby incorporated by reference herein.

The stapling head 12 of the stapler 10 is shown in more detail in FIGS. 2–5. Turning now to FIGS. 2–5, the stationary part 18 of the stapling head 12 includes a removable staple cartridge 30 which carries a double row of staples 32, each staple having its own driver 34. As seen best in FIG. 3, the staples 32 are arranged in two semi-circular rows with each row being staggered with respect to the other. It will be appreciated, however, that while the staples are preferably arranged in semicircular rows, the staple cartridge 30 preferably extends approximately two hundred to two hundred and twenty degrees around the circle in order to afford stability to the removable cartridge. A substantially semi-cylindrical stapling cam 36 is rotatably mounted below and behind the staple cartridge 30. The stapling cam has an inclined leading face 38, and a plurality of interior surface splines. According to one embodiment of the invention, a cutting knife 42 is coupled to the cam 36 at a distal interior portion thereof. The control wire 22, mentioned above, is coupled to a splined roller which engages the splined surface 40 of the stapling cam 36. Those skilled in the art will appreciate that rotation of the cable 22 will thereby cause rotation of the cam 36. Furthermore, as the cam is rotated, the inclined leading surface 38 will sequentially engage the drivers 34 of the staples 32 so that the staples are sequentially fired as the cam rotates. According to this embodiment, the knife 42 is arranged behind the leading surface of the cam so that tissue will be cut after it is stapled.

The movable part 20 of the stapling head 12 includes a semi-circular anvil 48 having a corresponding number of staple bending dimples 50. The movable part 20 is coupled to the stationary part 18 by means of a threaded post 52 having a longitudinal keyway 52*a*. Preferably, a convex mirror 54 is provided in the space between the post 52 and the anvil 48 to provide peripheral vision. If desired, the convex mirror can be provided with a central hole leading to a passage (not shown) in the movable part 20 which terminates in a transparent lens or portion (not shown) for distal viewing. Distal viewing is desirable in steering the endoscope with the stapler through the colon. Alternatively, the passageway with the transparent lens or window are provided in lieu of the mirror. It will be appreciated by those skilled in the art that the distal end 20*a* of the movable part 20 is preferably tapered to facilitate movement of the stapler through the lumen of the intestines. In this embodiment, the movable part is hemi-ovoid.

According to this first embodiment of the invention, the threaded post 52 of the movable part extends into the stationary part 18 and is engaged by an idler worm gear 58 mounted on an axle 60. In addition, a key 53 is provided in the stationary part 18 which engages the keyway 52*a* in the post 52 to prevent rotation thereof. The distal end of the control cable 24 is coupled to a worm gear 62 which engages the idler gear 58. Those skilled in the art will appreciate that rotation of the non-torsional cable 24 will thereby cause rotation of the worm gear 62 which will cause rotation of the idler gear 58. It will also be appreciated that rotation of the idler gear 58 will result in translation of the threaded shaft 52 either proximally or distally depending on the direction of rotation.

From the foregoing, it will be appreciated that the control wires 22, 24 are appreciably spaced apart from each other in order to accommodate the endoscope 16. Moreover, the distal end of the stationary part 18 is provided with openings 18*a*, 18*b* through which the optical elements of the endoscope may view the space between the stationary part 18 and the movable part 20 (and through the movable part, if a window is provided) and through which a flexible forceps (26 in FIG. 1) may pass. It will therefore be appreciated that the mirror 54 on the movable part 20 may aid in viewing the colon walls axially located between the stationary part 18 and the movable part 20 of the stapler.

Referring now to FIGS. 1–5 generally, those skilled in the art will appreciate that the endoscopic stapler of the invention is used in the following manner: After the stapler 10 is attached to the endoscope 16, the assembly is advanced transanally to the surgical site with the aid of the optics and steering means of the endoscope 16. Upon arrival at the surgical site, the forceps 26 are inserted through the instrument port of the endoscope and used to draw diseased tissue into the space between the movable part 20 and the stationary part 18 of the stapler. When sufficient tissue is in place, the control wire 24 is rotated to draw the movable part 20 proximally toward the stationary part 18 trapping tissue between the staple cartridge 30 and the anvil 48. When the movable part 20 and the stationary part 18 are tightly closed, the control wire 22 is rotated to sequentially fire a semi-circular double row of staples 32 around the diseased tissue and to sever the diseased tissue from the stapled tissue with the knife 42. The control wire 24 is then rotated in an opposite direction to slightly separate the movable part 20 from the stationary part 18 of the stapler so that the apparatus can be withdrawn from the intestine. The movable part 20 and the stationary part 18 of the stapler are opened more completely so that the diseased tissue can be removed. If a second surgical site is involved in the same procedure, the spent staple cartridge 30 is removed and replaced with a new staple cartridge and the apparatus is re-introduced transanally. Upon completing a single procedure, the stapler 10 is removed from the endoscope 16 and is appropriately disposed.

Figure 6:
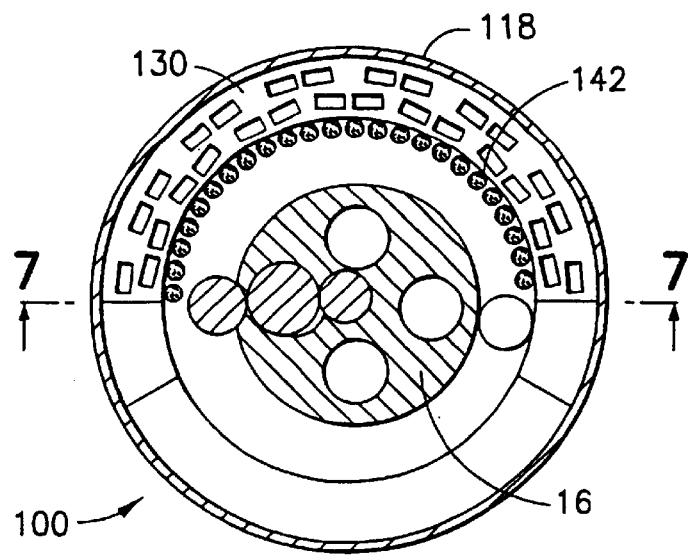
FIG. 6 is a view similar to FIG. 3 of an alternate first embodiment of the invention.
Figure 7:
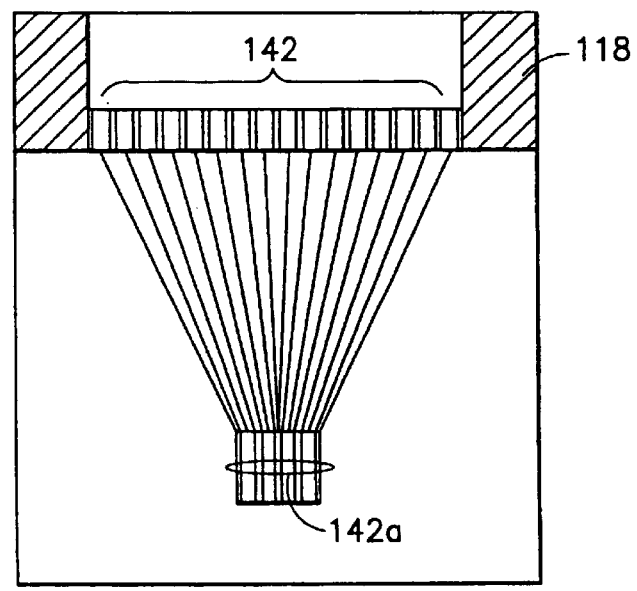
FIG. 7 is a sectional view taken along line 7—7 in FIG. 6.

Turning now to FIGS. 6 and 7, an alternate first embodiment of a stapler 100 according to the invention is substantially the same as the embodiment 10 with similar reference numerals referring to similar parts. In this embodiment, the knife is replaced with a semicircular array of fiber optics 142 which are optically coupled to a single optical path member 142*a*. The path member 142*a* is coupled to a controller source of laser radiation (not shown). The path member 142*a* may be fed through one of the lumena of the endoscope 16 or may be fed through a third outer lumen (not shown) of the sleeve 14 of FIG. 1. An advantage of this embodiment is that sclerotic diseased tissue may be cut with a minimum of effort.

Figure 8:
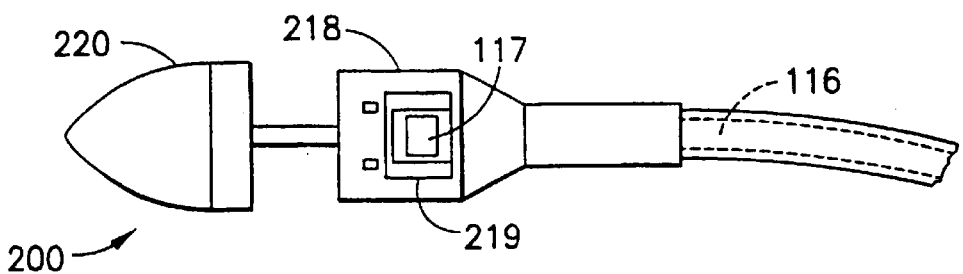
FIG. 8 is broken top view of the stapling head of a second alternative first embodiment of the invention.

Turning now to FIG. 8, a second alternate first embodiment of a stapler 200 according to the invention is substantially the same as the embodiment 10 with similar reference numerals referring to similar parts. In this embodiment, the stationary part 218 is provided with an upper optical window 216, and a side viewing endoscope 116 is used. The endoscope 116 is arranged so that its viewing port 117 is aligned with the window 219. An advantage of this embodiment is that the optics of the endoscope can be used when the movable part and the stationary part are in the closed position.

Figure 11:
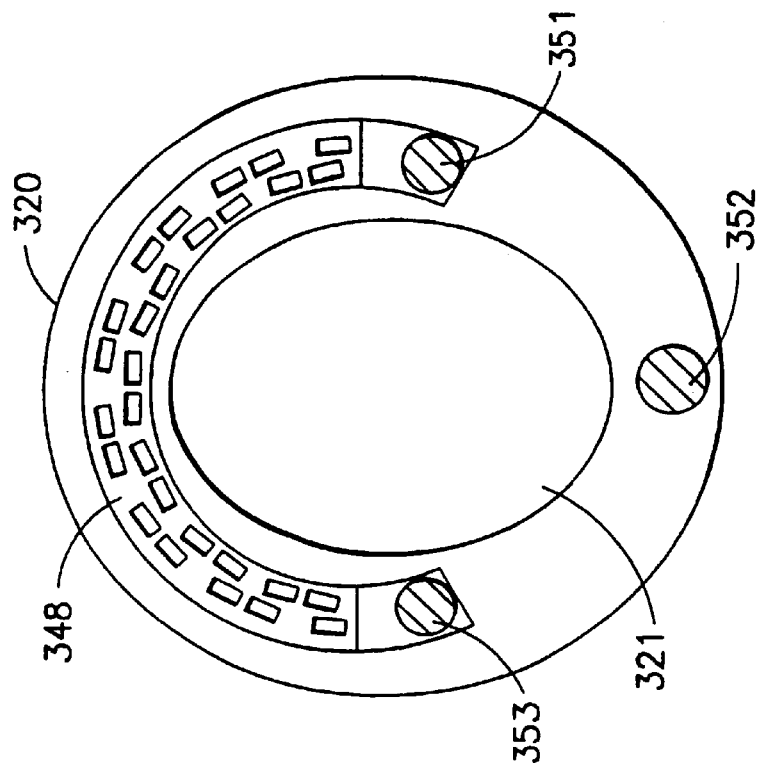
FIG. 11 is a view similar to FIG. 4 of the second embodiment of the invention.
Figure 10:
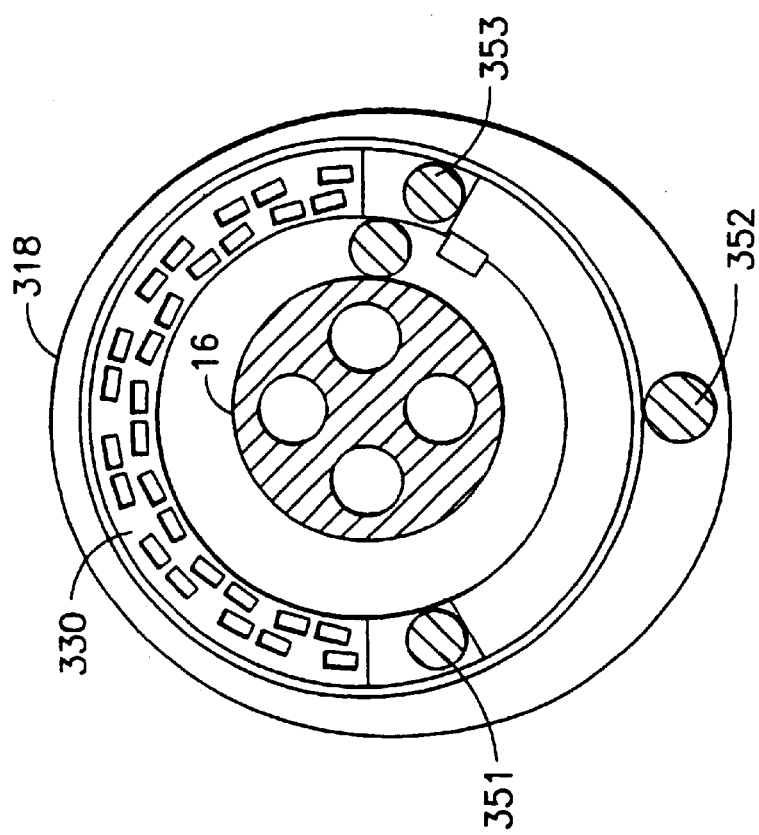
FIG. 10 is a view similar to FIG. 3 of the second embodiment of the invention.

FIGS. 9–11 show a second embodiment of a stapler 300 according to the invention which is somewhat similar to the embodiments described above with similar reference numerals referring to similar parts. In this embodiment, the movable member 320 is substantially ovoid and is coupled to the stationary member 316 by a lower threaded post 352 and two side stabilizing posts 351 and 353. Accordingly, the control wire 324 is located in the lower portion of the stationary member 318 and directly couples to the threaded post 352 via a worm gear 362. The advantage of this embodiment is that a clear path is provided for the distal end of the endoscope 16, and the coupling of the members 318 and 320 is more stable. Since the endoscope 16 may be located more distally, a recess 321 is provided in the movable member 320 to receive the distal end of the endoscope when the movable and stationary members are closed. The recess also permits the light from the fiber optics to be transmitted through the movable member 320, which preferably includes a lens or transparent window at its distal end. If desired, a mirror (not shown) may be provided in the recess 321 as discussed above with reference to the embodiment of FIGS. 1–5.

As shown in FIG. 9a, the embodiment of FIGS. 9, 10, and 11 may also be used with an endoscope which can be moved relative to the stapler such that the distal end of the endoscope can be articulated between the stationary and moving parts of the stapler. In this manner, a more direct view of the colon wall can be obtained, and the endoscopic forceps is naturally directed in an appropriate position for grasping and pulling tissue into the stapler area when the endoscope is partially withdrawn from its position shown in FIG. 9a back into the stapler (such as shown in FIG. 9). Movement of the endoscope relative to the stapler can be accomplished by providing the stapler tube with a central lumen which is somewhat larger than the endoscope, thereby reducing friction and providing clearance (i.e., an annular space is provided between the endoscope and stapler tube). At the same time, the movable portion 320 of the stapler head is preferably provided with a recess 321a which will receive the distal end of the endoscope. Thus, by pushing the endoscope forward into recess 321a, both the endoscope and stapler can be advanced, with the endoscope pushing the stapler forward. When the endoscope is pulled proximally a short distance, the stapler will remain in position, and the endoscope can be directed as desired. The forceps can then be used to pull tissue into the stapler, with the endoscope and forceps being further retracted into the stapler. After the stapling procedure, the endoscope and stapler can be removed from the patient by grasping both together at the proximal end and withdrawing them together.

FIGS. 12 and 12a show an alternate second embodiment of a stapler 400 according to the invention which is somewhat similar to the embodiments described above with similar reference numerals referring to similar parts. In this embodiment, a larger recess 421 is provided in the movable member 420 to receive the distal end of a side viewing endoscope 116 when the movable and stationary members are closed. A suitable side viewing endoscope having a radially directed forceps port is described in U.S. Pat. No. 4,646,722 to Silverstein et al., the complete disclosure of which is incorporated by reference herein.

FIG. 13 shows a third embodiment of a stapler 500 according to the invention which is somewhat similar to the embodiments described above with similar reference numerals referring to similar parts. In this embodiment, the movable member 520 is provided with a through bore 521 to allow the endoscope 16 to pass through the stapling head and bend proximally to view the surgical site.

Figure 14A:
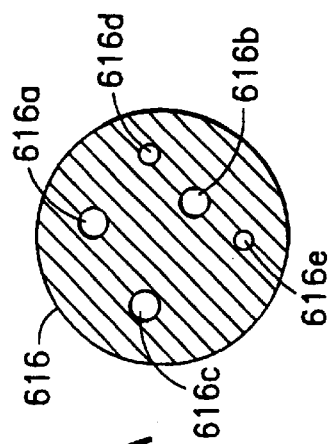
FIG. 14a is a sectional view taken along line 14A—14A in FIG. 14.
Figure 14:
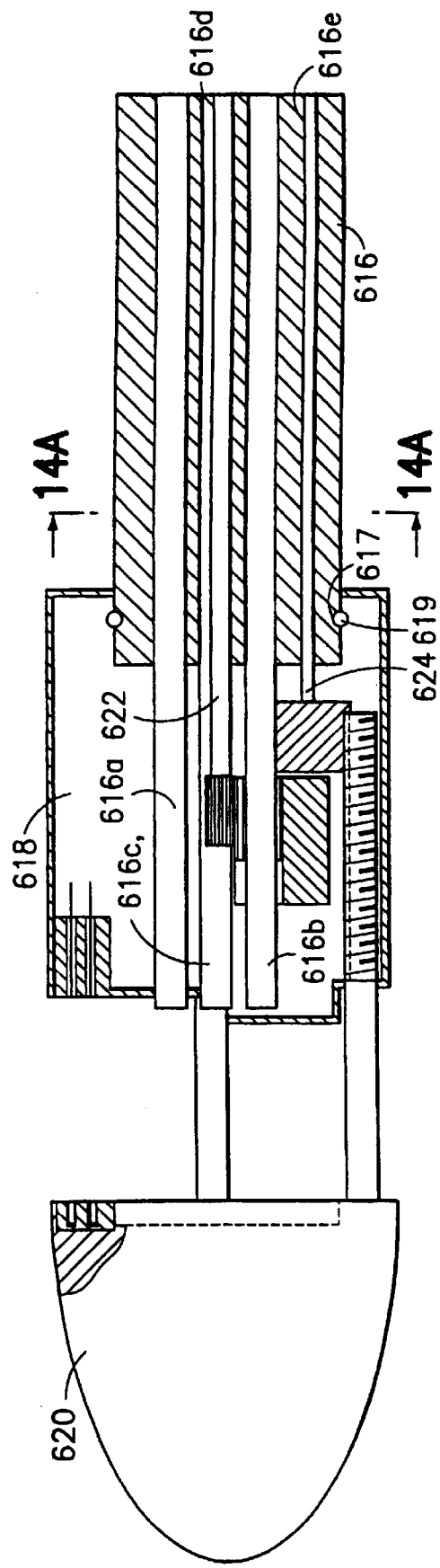
FIG. 14 is a view similar to FIG. 12 of a fourth embodiment of the invention.

FIG. 14 shows a fourth embodiment a stapler 600 according to the invention which is somewhat similar to the embodiments described above with similar reference numerals referring to similar parts. This embodiment is designed for use with a special endoscope 616 having optical ports 616a, 616b, an instrument (forceps) port 616c, and ports 616d and 616e which carry the control wires 622, 624. The distal end of the endoscope is provided with a groove 617 and the proximal end of the stationary member 618 is provided with a mating coupling device 619. As shown, the ports 616a–616c extend beyond the distal end of the endoscope as rigid tubes to reach the space between the stationary part 618 and the movable part 620 of the stapler and the control wires are removable from the ports 616d, 616e when the endoscope is removed from the stapler.

Turning now to FIGS. 15 and 15a, a fifth embodiment of the a stapler 700 according to the invention is somewhat similar to the fourth embodiment described above with similar reference numerals referring to similar parts. Here, the stationary part 718 has a threaded proximal end 719, includes two optical paths 776a, 776b, and an instrument port 776c. The optical paths and the instrument port have curved distal ends which direct them toward the opening through which tissue will be drawn. The proximal ends of the optical paths and the instrument port have hollow ends for coupling to optical paths and the instrument port of the endoscope 716. In this embodiment, the distal ends of the control wires 722 and 724 are rigid and terminate inside the stationary part 718 with coupling ends such as a keyway or hex socket coupling. The endoscope 716 has a rotatable threaded collar 717 which mates with the threaded end 719 of the stationary part 718. The optical ports 716a, 716b of the endoscope 716 extend rigidly beyond the distal end of the scope and mate with the hollow ends of the optical paths 776a, 776b in the stationary part. Similarly, the instrument port 716c of the endoscope 716 extends rigidly beyond the distal end of the scope and mates with the hollow end of the instrument port 776c in the stationary part 718. The control wires 722', 724' carried in the lumens 716d, 716e of the endoscope 716 terminate with rigid connectors (keyed or hex connectors) which mate with the coupling ends of the control wires 722 and 724 inside the stationary part 718. The stationary part 718 is thereby coupled to the endoscope 716 by aligning the ports and control wires, pressing the endoscope and the proximal end of the stationary part together and twisting threaded collar 717 onto the threaded end 719 of the stationary part. It will be appreciated that the endoscope is easily removed from the stapler by reversing these steps.

There have been described and illustrated herein several embodiments of an endoscopic stapler. While particular embodiments of the invention have been described, it is not intended that the invention be limited thereto, as it is intended that the invention be as broad in scope as the art will allow and that the specification be read likewise. Thus, while a semicircular stapling pattern has been disclosed, it will be appreciated that an arced pattern of less than 180° could be utilized. Also, while a double row of staggered staples has been shown, it will be recognized that a single row, or multiple rows of other configurations could be used with similar results obtained. Moreover, while particular configurations have been disclosed in reference to a mirror being located on the movable portion of the stapler head, it will be appreciated that other configurations could be used as well. For example, the mirror may be movable, rotatable, or hinged to permit forward viewing while the endoscope and stapler are being steered through the colon, and to permit peripheral viewing of the colon walls when the endoscope and stapler are roughly in place. Also, while various embodiments of the invention have been shown with optical windows on the distal end and proximal side of the stapler head, other configurations of optical windows can be used. Furthermore, while a particular stapler tube with two small lumena, a large lumen and a slit have been shown, it will be understood that stapler tubes having a greater number of lumena, with different placement, and with or without a slit, may be utilized. Further yet, while the stapler head has been described with reference to specific gear configurations and placement, other configurations can be used to achieve similar results. For example, the rotating cam with a splined inner surface can be replaced with a rotating cam having a splined outer surface provided the driving gear is located accordingly.

Those skilled in the art will further appreciate that while the apparatus of the invention was described with reference to a full thickness resection of the colon, it will be appreciated that the apparatus can be utilized other digestive tract transluminal procedures, and can be introduced transorally as well as transanally. Also, while certain embodiments of the invention have been described with reference to custom endoscopes, it will be appreciated that the specific configurations of the custom endoscopes/stapler embodiments may be varied. For example, different arrangements of lumena and control wires, and different coupling means for coupling the control wires to the driving gears may be provided with similar results obtained. It will therefore be appreciated by those skilled in the art that yet other modifications could be made to the provided invention without deviating from its spirit and scope as so claimed.

What is claimed is:

1. An endoscopic stapling system comprising:

a stapling head adapted to be coupled to a distal end of a flexible endoscope, said stapling head having a stationary part and a movable part, said stapling head containing an anvil and a staple firing mechanism for firing staples into said anvil; and a transmission mechanism adapted to extend from a proximal end of the endoscope to said moveable part, said transmission mechanism including a gear connected to a distal end of a flexible shaft.

2. A stapler according to claim 1, wherein:

said staple firing mechanism is contained in said stationary part, and said anvil is contained in said moveable part.

3. An endoscopic stapler for use with an endoscope, said stapler comprising:

a stapling head having a stationary part and a moveable part, said stapling head containing an anvil and means for firing staples into said anvil, wherein the means for firing are contained in said stationary part and the anvil is contained in said movable part;

means for coupling said stapling head to the endoscope; and means for moving said movable part relative to said stationary part, wherein said means for moving further includes a torsionally rigid wire for turning a gear and wherein said movable part and said stationary part are coupled to each other by a shaft that engages said gear.

4. A stapler according to claim 3, wherein:

said torsionally rigid wire is adapted to be coupled at a proximal end of the endoscope to means for twisting said torsionally rigid wire.

5. An endoscopic stapling system comprising:

a stapling head adapted to be coupled to a distal end of an endoscope, said stapling head having a stationary part and a movable part, said stapling head containing an anvil and a staple firing mechanism for firing staples into said anvil, and a transmission mechanism including a gear connected to a distal end of a flexible shaft adapted to extend between a proximal end of the endoscope and said moveable part.

6. An endoscopic stapling system comprising:

a stapling head adapted to be coupled to a distal end of a flexible endoscope, said stapling head including an anvil member and a staple firing mechanism for firing staples into the anvil member, said anvil member and said staple firing mechanism coupled together and movable relative to one another, and a transmission mechanism extending between a proximal end of the endoscope and said stapling head, said transmission system including a gear connected to a distal end of a flexible shaft adapted to extend from said stapling head to the proximal end of the endoscope.

7. The endoscopic stapling system according to claim 6, wherein said transmission system, in an operative configuration, is adapted to transmit force from the proximal end of the endoscope to said stapling head to move said anvil member and said staple firing mechanisms between a stapling position and a tissue receiving position.

8. The endoscopic stapling system according to claim 6, wherein said shaft is flexible.

* * * * *